United States Patent
Nyfors et al.

(10) Patent No.: US 6,915,707 B2
(45) Date of Patent: Jul. 12, 2005

(54) COMPACT FLOW METER

(75) Inventors: Ebbe Nyfors, Sandnes (NO); Øystein Lund Bø, Randaberg (NO)

(73) Assignee: Roxar Flow Measurement AS, Stavanger (NO)

(*) Notice: Subject to any disclaimer, the term of this patent is extended or adjusted under 35 U.S.C. 154(b) by 0 days.

(21) Appl. No.: 10/492,348

(22) PCT Filed: Oct. 1, 2002

(86) PCT No.: PCT/NO02/00349

§ 371 (c)(1),
(2), (4) Date: Apr. 13, 2004

(87) PCT Pub. No.: WO03/034051

PCT Pub. Date: Apr. 24, 2003

(65) Prior Publication Data

US 2004/0244501 A1 Dec. 9, 2004

(30) Foreign Application Priority Data

Oct. 19, 2001 (NO) .......................................... 20015132

(51) Int. Cl.[7] .............................................. G01F 1/44
(52) U.S. Cl. ................................................ 73/861.63
(58) Field of Search ..................... 73/861.04, 861.02, 73/861.63, 861.64

(56) References Cited

U.S. PATENT DOCUMENTS

| | | | |
|---|---|---|---|
| 4,776,210 A | 10/1988 | Baillie et al. | |
| 4,888,547 A | 12/1989 | McGinn et al. | |
| 5,103,181 A | 4/1992 | Gaisford et al. | |
| 5,793,216 A | 8/1998 | Constant | |
| 5,949,237 A | * 9/1999 | Berger et al. | ............... 324/636 |
| 6,332,111 B1 | * 12/2001 | Fincke | ........................ 702/50 |
| 6,655,221 B1 | * 12/2003 | Aspelund et al. | ........ 73/861.04 |

FOREIGN PATENT DOCUMENTS

| | | |
|---|---|---|
| NO | 310322 B1 | 7/2000 |
| RU | 2164340 C2 | 3/2001 |
| WO | WO 99/10712 A1 | 3/1999 |
| WO | WO 00/02017 A2 | 1/2000 |
| WO | WO 0045133 | 8/2000 |
| WO | WO 00/45133 A1 | 8/2000 |

OTHER PUBLICATIONS

Nyfors, E., et al. *Industrial Microwave Sensors*, 1989, page(s), 10–21, 134–141 and 164–187, Artech House, Norwood.

Nyfors, E., *Cylindrical Microwave Resonator Sensors for Measuring Materials Under Flow*, Thesis, Helsinki Univ. Of Tech., Radio Lab. Report S243, May 2000, pages(s) 23–29, 30–34, 40–42, 46–61, 85–95, 125–126, 131–132, 139, 148–149 and 163–166.

* cited by examiner

*Primary Examiner*—Edward Lefkowitz
*Assistant Examiner*—Jewel Thompson
(74) *Attorney, Agent, or Firm*—Rothwell, Figg, Ernst & Manbeck (57) ABSTRACT

Apparatus for measuring the composition and flow rate of a fluid (1) comprising a mixture of e.g. oil and water in a pipe (2), wherein an integrated mechanical structure (3) serves as a microwave resonator sensor for providing permittivity measurements and where the mechanical structure also functions as a differential pressure element for providing flow rate measurements.

22 Claims, 6 Drawing Sheets

COMPACT FLOW METER

This invention relates to a compact flow meter for measuring the composition or flow rates of individual components of a fluid.

BACKGROUND

In the oil industry there is in various situations a need to measure the composition or flow rates of individual components of a fluid, which is a mixture of oil and water and possibly gas, flowing in a pipe. Such measurements are needed e.g. to determine what an oil well produces and thus be able to control the production for optimal recovery. Measurements are also needed for monitoring the performance of production separators, control of the injection of chemicals (prevention of the development of scale, corrosion, or hydrate), or for managing the flow regime, when the fluid has to be transported a long distance in a pipeline.

The conventional technique is to separate the fluid in a separator and measure the flow of each of the components separately. During the last few years so-called multiphase meters have also become available, which measure the composition and the flow rates without prior separation [1]. A special case of a multiphase flow is the so-called wet gas flow, which usually means that the GVF (gas void fraction) is roughly GVF>95%. The relative accuracy, which is achievable for the rates of the liquid components, is too low for most applications in the case of a wet gas flow, when measured with multiphase meters.

STATE OF THE ART

In the text below the following definition of terminology will be used:

meter a complete measuring device including sensor(s) and necessary electronics and software sensor a sensing element of a meter (approximate synonym: transducer)

The flow rates of the components of a multiphase flow can be measured with a test separator or a multiphase meter. The test separator is expensive and bulky. Therefore it is not practical to have a test separator measuring the production continuously on every well, but rather one test separator per oil field. This is especially true at offshore installations. Each well is routed through the test separator at regular intervals. When a well is routed through a test separator, the conditions for the well change, which may influence the production so that the measurement does not represent the average production correctly. A test separator is also slow because of the long settling time, especially in the case of a wet gas flow.

Multiphase meters measure the composition of the flow and the flow speed separately. From these the flow rates are calculated. Multiphase meters can be installed for the continuous, on-line measurement at every location, where measurements are needed. An important application is to install the meter subsea in the seabed production system, which is mainly a skid mounted on top of a subsea well. If each well in a cluster of wells is equipped with a subsea multiphase meter, one common pipeline can be used to tie the cluster of subsea wells to a production platform, which may be located tens of kilometres from the cluster. The space available for a multiphase meter in a seabed production system is limited. A compact design is therefore an advantage.

A multiphase meter measures four quantities, i.e. the flow speed and the relative fractions of the three components (oil, water, and gas). It usually also needs the temperature, pressure, density of the oil and gas, and the water salinity as input parameters for compensational purposes, but these will be ignored in the following discussion of the main measurements. Theoretically such a system can be characterized by a set of four equations, of which one equation is that the sum of the three components is 100%. Hence a multiphase meter must be based on the use of at least three independent measurements. There are several known measurement principles, which can be used in various combinations in multiphase meters. E.g. microwaves or capacitive technology can be used to measure the permittivity of the flow. Because the permittivity of the flow depends on the permittivity of the components (which can be considered known) and the composition, the permittivity of the flow contains information about the composition. The permittivity is especially sensitive to the water content. Various kinds of densitometers can be used to measure the density of the flow. Gamma radiation of several energy levels can be combined to yield information about the composition. Cross-correlation techniques or DP (differential pressure) measurements over a restriction in the flow can be used to measure the flow speed. There are a number of multiphase meters on the market. They are based mainly on various combinations of the measurement principles mentioned above. They have been designed to cover the whole range of compositions, which has required compromises making them less suitable and less accurate for the special case of wet gas flow measurements.

Ordinary multiphase meters can be used with wet gas flow if they are preceded by a partial separator, which reduces the GVF. This solution is, however, expensive and also bulky, and therefore not suitable for subsea applications. Of the measurement principles that were mentioned above, cross-correlation methods, densitometers, and multi-energy gamma ray methods are not well suited for wet gas meters because of their low sensitivity. The best concept for a wet gas meter therefore seems to be to use a microwave sensor to measure the permittivity of the flow, and a DP method to measure the mass flow. The best sensitivity is achieved if the microwave sensor is a resonator [2,Ch.3]. A PVT (Pressure-Volume-Temperature) software package can be used to separate the liquid and gas content of the hydrocarbons (oil+gas), if needed. A PVT software is an equation of state based program used for simulation and matching of PVT experiments. Such software packages are typically used to calculate the temperature and pressure dependent individual densities of the gas and liquid phases and the gas/liquid ratio of a fluid with known molecular composition. A PVT program requires information about the temperature, the pressure, and the molecular composition of the fluid. These values may be assumed to be known quantities. Alternatively, the temperature and pressure may be obtained from sensors positioned in or at the fluid and could be integrated in the apparatus.

Because a wet gas flow tends to form an annular flow regime (liquid along the wall of the pipe and gas in the middle) a mechanical flow mixer is most likely also necessary. Therefore a wet gas multiphase meter would comprise a flow mixer, a DP element, and a microwave resonator. A spool piece with these components mounted in series is inconveniently long for mounting in a seabed production system for subsea applications.

OBJECTIVES

It is a purpose of the present invention to provide an improved apparatus to avoid the above-mentioned limitations of the performance of presently known techniques.

It is another purpose of the invention to provide a single structure for performing both microwave and DP-measurements, and for mixing the flow.

It is yet another purpose to provide a single structure for performing both microwave and DP-measurements, and for mixing the flow, that is compact in design in order to be easier to design into e.g. subsea installations, and less expensive to manufacture.

It is a further objective to provide a single, compact structure for performing both microwave and DP-measurements, and for mixing the flow, which is smaller, mechanically simpler, and less expensive to manufacture and suitable for measurements in a two-phase flow.

It is yet a further objective to provide a single, compact structure for performing both microwave and DP-measurements, and for mixing the flow which is smaller, mechanically simpler, and less expensive to manufacture and suitable for measurements in a three-phase flow, in particular for wet gas flow.

The objectives stated above are obtained by providing an apparatus for measuring the composition and flow rate of a fluid in a pipe, wherein an integrated mechanical structure serves as a microwave resonator sensor and as a differential pressure element for providing permittivity and flow rate measurements, respectively.

Preferres embodiments of the apparatus according to the invention are defined in the independent claims.

DETAILED DESCRIPTION OF INVENTION

A detailed description of the invention will be given below. The application of the V-cone design as a wet gas meter is used as an example. The following figures are used in the description:

Figure 3:
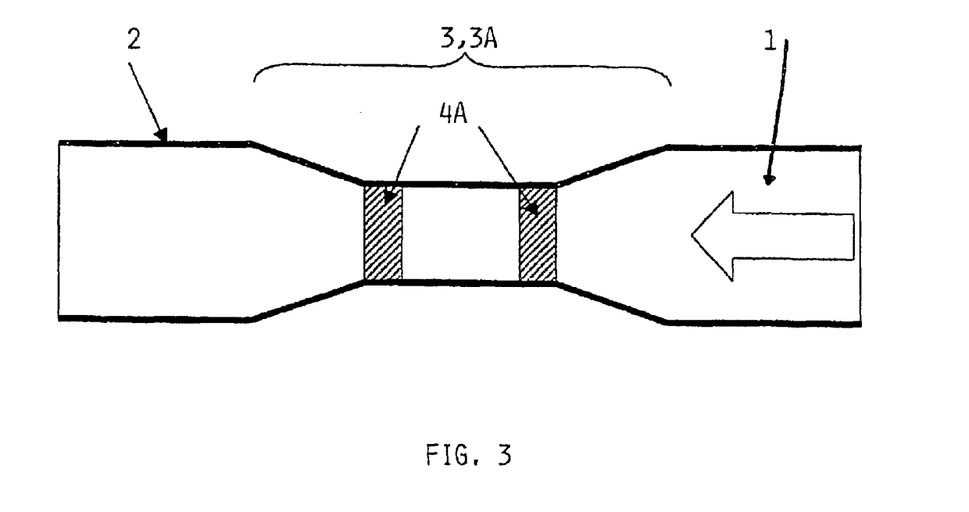
FIG. 3 A venturi tube with end grids in the throat. The space between the grids is a microwave cavity resonator.

FIG. 3 illustrates one example of a short, mechanically simple, integrated mechanical structure that can be used both as a microwave resonator sensors and as a differential pressure element. The flow of a fluid 1 in a pipe 2 is illustrated by the direction of the arrow. The fluid encounters an integrated mechanical structure 3 which serves as a microwave resonator sensor and as a differential pressure element for providing permittivity and flow rate measurements.

In order to explain the invention in more detail a discussion of the principles behind the invention follows.

The Permittivity of a Fluid Mixture

When two material components (A and B), (liquid, gas, or solid particles), with different permittivity ($\epsilon_A$ and $\epsilon_B$) are mixed, the mixture has a permittivity $\epsilon_m$ that is dependent on the mixing ratio $\Phi$ of the two components [2, Ch. 2]. The mixing ratio is usually expressed as the total volume of one of the components relative to the volume of the mixture, e.g.

$$\Phi_A = \frac{V_A}{V_A + V_B} \qquad (1)$$

where $V_A$ is the volume of component A and $V_B$ is the volume of component B in a sample of volume $V_m = V_A + V_B$ of the mixture. If e.g. A is water and B is oil, $\Phi_A$ is the water content or WVF (water volume fraction) of the mixture. In the case of the fluid produced in an oil well, B may in turn be a known mixture of oil and gas, and will therefore be generally called the hydrocarbon component. The way $\epsilon_m$ depends on $\Phi$ depends on how the components mix with each other and is therefore specific for these components. As a model for this dependence a known model [2, Ch. 2.4] may be used, or an empirical calibrated model. By using this model, $\Phi$ can then be derived from a measured value of $\epsilon_m$.

In the general case the permittivity is a complex quantity, i.e. it has a real and an imaginary part:

$$\epsilon_m = \epsilon'_m - j\epsilon''_m \qquad (2)$$

Physically the real part gives the effect of the medium on the speed of propagation, change of phase, and wavelength compared to vacuum, while the imaginary part tells how fast the energy of a propagating wave is dissipated. Both parts depend on the composition, but such that the imaginary part is mostly sensitive to lossy components in the mixture, like for example the salinity of the water in a mixture.

The Measurement of the Permittivity Using a Microwave Resonator.

For the measurement of $\epsilon_m$, a microwave resonator can be used as a sensor. Such a sensor has a resonant frequency that is dependent on the permittivity of the medium with which it is filled. If $f_0$ is the resonant frequency of the sensor, when it is empty, and $f_m$ when it is filled with a fluid mixture, the real part of the permittivity of the mixture is [2, p. 133]

$$\varepsilon'_m = \left[\frac{f_0}{f_m}\right]^2 \qquad (3)$$

In addition to the resonant frequency the resonance is characterised by the quality factor, which is a measure of how fast the stored energy is dissipated due to various loss mechanisms, and therefore depends on the imaginary part of the permittivity of the mixture. A high quality factor means that the resonance peak is narrow and well defined. By measuring both the resonant frequency and the quality factor, two partly independent measurements are obtained. For example including the measurement of the quality factor in a meter therefore brings the possibility of also measuring the salinity of the water in a mixture of water and hydrocarbons. This function has special applications in the petroleum industry, e.g. for detecting the break through of formation water, or injected water.

Basics of Microwave Resonators

The basics of microwave resonators have been described in e.g. [2,Ch.3],[3,Ch.3], and [4, Ch.7]. All microwave resonators that are normally used as sensors, can be thought of as formed by a section of transmission line bounded by impedance discontinuities in both ends. The transmission line can be made of any kind of structure supporting electromagnetic waves, such as hollow waveguide, coaxial line, slotline, stripline, dielectric waveguide, or two-conductor line. The role of the impedance discontinuities is to cause the propagating wave to be reflected. Where the transmission line is open-circuited, the reflection coefficient is Γ=+1 (i.e. phase angle φ=0), and where the line is short-circuited, Γ=−1 (φ=π). If the impedance discontinuity differs from those mentioned, or purely reactive terminations ($|\Gamma|=1$, $\phi \ne 0$ & $\pi$), the reflection will be partial ($0 \le |\Gamma| \le 1$) and the resonator leaky. A leakage of energy reduces the quality factor of the resonator and makes the resonance peak broader, which usually makes the resonator less attractive as a sensor.

The field in the resonator is excited by the external circuit through some kind of coupling, which may be for example an aperture (small hole), coupling loop, coupling probe, or coupling through the leaky ends. The coupling device radiates a wave into the resonator. The wave propagates along the transmission line and is reflected in alternating directions at the discontinuities. Resonance occurs, i.e. the resonance condition is fulfilled, if the exciting field is in phase with the reflected components. Hence, they will interfere constructively and destructively to give a standing wave pattern. This will happen only at certain frequencies (resonant frequencies). A standing wave with a strong field will build up, thus storing a great amount of energy. Equilibrium is reached at the level where the loss power in the resonator (in the metal or dielectric, by radiation, or by escaping through the couplings) equals the excitation power. At resonance, the energy alternates between the electric field and the magnetic field, which contain the same amount of energy.

The resonance condition is fulfilled, when the mode wavelength compared to the dimensions of the resonator take on specific values. These values depend on the kind of termination, which bounds the resonator. The reflected wave components are in phase with the exciting field if the total phase change experienced by the wave on its way back and $$\frac{2\pi}{\lambda} \cdot 2L + \varphi_1 + \varphi_2 = n \cdot 2\pi \tag{4}$$

forth along the transmission line, is a multiple of 2π: where L is the length of the transmission line, $\phi_1$ and $\phi_2$ are the phase angles of the reflection coefficients, and n is an integer. The first term on the left hand side of (4) is the phase change of the wave on its way back and forth. Equation (4) can be written in the form $$L = \left(\frac{n}{2} - \frac{\varphi_1 + \varphi_2}{4\pi}\right)\lambda \tag{5}$$

If the resonator is open-circuited at both ends, $\phi_1=\phi_2=0$, and (5) gives for the length:

$$L = \frac{n\lambda}{2} = \frac{\lambda}{2}, \lambda, \frac{3\lambda}{2}, \tag{6}$$

If the resonator is short-circuited at both ends, $\phi_1=\phi_2=\pi$, and the same result as above is obtained:

$$L = \left(\frac{n}{2} - \frac{1}{2}\right)\lambda = \frac{\lambda}{2}, \lambda, \frac{3\lambda}{2}, \tag{7}$$

If the resonator is short-circuited at one end and open-circuited at the other, $\phi_1=\pi$ and $\phi_2=0$, and (5) gives $$L = \left(\frac{n}{2} - \frac{1}{4}\right)\lambda = \frac{\lambda}{4}, \frac{3\lambda}{4}, \frac{5\lambda}{4}, \frac{5\lambda}{4}, \tag{8}$$

For each situation, there is an infinite number of solutions satisfying the resonance condition. Therefore, each resonator has an infinite number of resonant frequencies for each wave mode. The lowest resonance is at the frequency for which the wavelength is two or four times the length of the resonator, depending on the terminations.

For exact calculation of the resonant frequency, the relation between wavelength and frequency must be known. For TEM waves (in coaxial or other line with minimum two conductors) the relation is very simple. Because they have no cut-off frequency, the wavelength in the transmission line is the same as that of a plane wave in the same dielectric medium. In hollow waveguides the relation is slightly more complicated, because the wavelength of the waveguide mode is always longer than that of the corresponding plane wave:

$$\lambda_{wg} = \frac{\lambda_{pw}}{\sqrt{1 - \left(\frac{f_c}{f}\right)^2}} \tag{9}$$

where $\lambda_{wg}$ is the wavelength in the waveguide, $\lambda_{pw}$ is the wavelength of the corresponding plane wave, and $f_c$ is the cut-off frequency of the wave mode in the waveguide. In the case of waveguides with a cut-off frequency, the wavelength $\lambda_{wg}$ should be used in (4)–(8).

Equation (9) shows that $\lambda_{wg}$ becomes infinite at the cut-off frequency. In this situation also n=0 is a possible solution of (4), if the structure can support the wave mode in question. If a section of hollow waveguide is short-circuited in both ends, it can support TM modes. The resonant frequency is $f_r=f_c$ in such cases, independent of the length of the resonator. The field pattern then lacks structure in the axial direction of the resonator. TE waves can not exist with n=0, when the ends are short-circuited, because the transverse electric field must be zero at the ends. If the ends are open-circuited, the structure can support TE modes with n=0, but not TM modes, because they have an axial electric field, which must terminate at a metal surface.

Because an open circuit in a hollow waveguide is not as exact in location as a metal wall, there will be "end-effects" with fringing fields, but in practice the resonant frequency of such TE modes is very close to the cut-off frequency. For a better understanding of concepts like permittivity, waveguides, wave modes, TE, TM, TEM, cut-off frequency, etc., please refer to the references [2,Ch.1–3], [3,Ch.3],[4, Ch.7], [6], and [7].

The resonant frequency and the quality factor of a resonator can be measured using basically two different methods: The method of reflection coefficient and the method of transmission coefficient [3, Sec. 3.5]. When the former method is used, only one coupling probe is needed, while the latter method requires two probes.

Microwave Resonator Sensors in Pipes

When a microwave resonator sensor is implemented in a pipe for the purpose of measuring the permittivity of the fluid that is flowing in the pipe, the discontinuities must have a structure that is open enough so that the fluid can pass through the sensor. One practical type of discontinuity is an increase in the cut-off frequency [5], [6]. If the resonant waveguide has a cut-off frequency that is lower than that of the pipe, and the resonant frequency of the used mode is the same as the cut-off frequency, the energy can not propagate in the pipe. No other reflecting discontinuity is therefore needed. This allows structures that are very open for the flow to be used. The fin sensor is a good example of such a structure [6]. Another practical discontinuity is a grid, with so small holes that the energy cannot escape [7], [8].

Microwaves can propagate along a large variety of structures. There is no reason why the structure should even be uniform. Therefore the cross section of the resonant structure inside the pipe can be different at different locations along the structure. In the case of nonuniform structures the wave mode is inhomogeneous and can generally neither be described by any wave modes known from the literature nor be solved analytically. In such cases the resonant frequencies and field distributions can be solved approximately by numerical methods using e.g. FEM (finite element method) software. Any structure with a resonant frequency that is lower than the cut-off frequency of the pipe can in principle be used as a resonator sensor.

Figure 1:
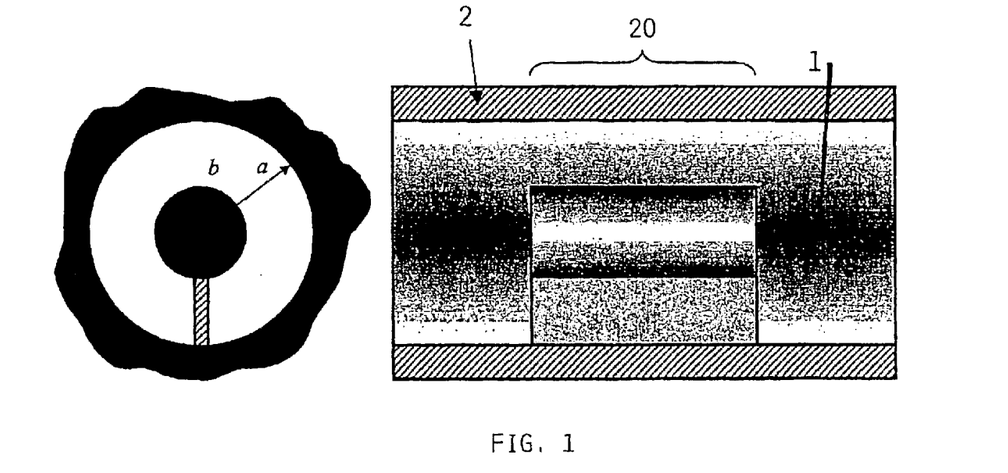
FIG. 1 A semisectorial microwave resonator.

Two examples of possible structures will be given here. The first one is the so-called semisectorial structure, which has been described in [3], [6], and [7]. FIG. 1 shows an example of a semisectorial structure 20. It has been shown in [3] that such a structure supports a TE mode, which has a cut-off frequency, which is lower than that of the pipe alone. Because the structure is open in the ends, the resonant frequency equals the cut-off frequency of the semisectorial section. Therefore the energy cannot escape into the pipe 2 and the structure is usable as a resonator sensor.

Figure 2:
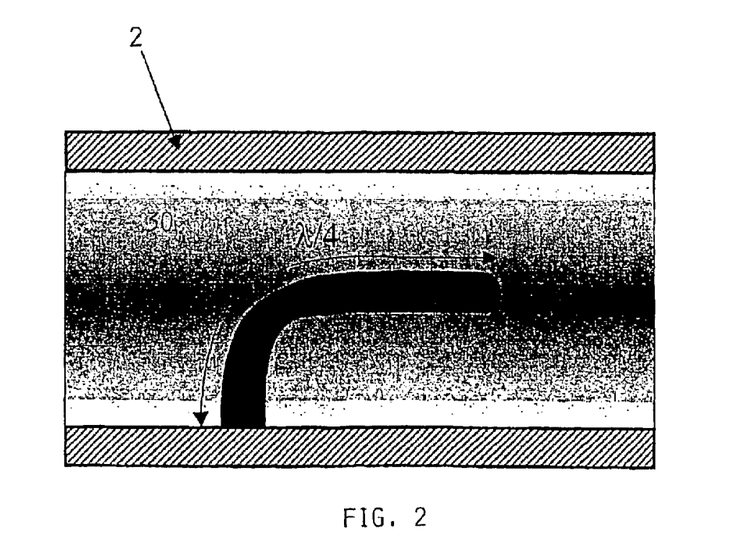
FIG. 2 A general resonating structure in a pipe. The structure is short-circuited to the wall in one end, and open in the other end.

FIG. 2 shows another possible resonant structure. It is a bent metal rod 30 that is shorted to the wall of the pipe 2 in one end and open in the other end. According to Eq. (8) it will have a first resonant frequency at a wavelength, where the rod is $\lambda/4$ long. Because of the nonuniform structure the resonant frequency is difficult to predict exactly, but can be found approximately by numerical methods. If the rod is made long enough the resonant frequency will be lower than the cut-off frequency of the pipe 2, in which case the structure can be used as a resonator sensor.

Basics of DP Mass Flow Measurements

Any nonuniform section of the pipe 2 will result in a change of the flow speed. Based on the theory of fluid dynamics a change of flow speed is known to cause a change of the pressure. This differential pressure is related to the mass flow. Therefore a measurement of the differential pressure (DP) caused by a nonuniform section of the pipe can be used to derive the mass flow. The most frequently used structures (DP elements) for DP measurements are the venturi tube, i.e. a section of pipe with smaller diameter than the rest of the pipe, and the orifice plate. Mass flow measurements with such structures have been described in the international standard ISO 5167-1 [9].

A special kind of DP element is the V-cone, which has been described in [10].

When using DP measurements to find the mass flow of the individual components in a two- or multi-phase flow, the standard formulas should generally be corrected for the appearance of slip, which means that the gas and liquid travel with slightly different speed. This is usually done by the introduction of so-called two-phase multipliers that are functions of the individual fractions and density of each of the components [11,Ch.11]. Hence, a measurement of composition, e.g. water, oil and gas content, of the fluid in combination with a DP measurement will improve the mass flow measurement in two- or multiphase flows.

EXAMPLE EMBODIMENTS OF THE INVENTION

A number of example embodiments of the integrated mechanical structure 3 of the invention which can be used both as microwave resonator sensors and as differential pressure elements will be further detailed below.

In all the embodiments it is assumed that microwave probe outputs and differential pressure outputs are input to a microprocessor or computing means using standard interface means and interfacing techniques. For simplicity the exact positioning of the probes in the apparatus is not detailed in the Figures, however, it will be understood, particularly when considering the references, that a large number of possibilities for positioning the probe means exist.

The microprocessor means or computing means typically may be adapted for running a PVT software program. Further, the microprocessor means or computing means may comprise standard display means, standard input and output means, and standard data storage means of well known types.

Venturi Tube

The integrated mechanical structure illustrated in FIG. 3 comprises a portion of the pipe being formed as a Venturi tube 3A. If additional mechanical elements 4, for example in the shape of grids 4A, are added to a venturi tube it will also work as a microwave resonator. The grids 4A can be designed so as not to obstruct the flow more than necessary, i.e. not to interfere with the DP measurement, and still confine the microwaves [3], [8]. There are many possible variations as to where the grids 4A can be mounted. If they are mounted in the throat (the narrow part) of the Venturi tube, as shown in FIG. 3, the microwave resonator will be a standard cylindrical end grid cavity resonator [3, Ch. 7].

Figure 4:
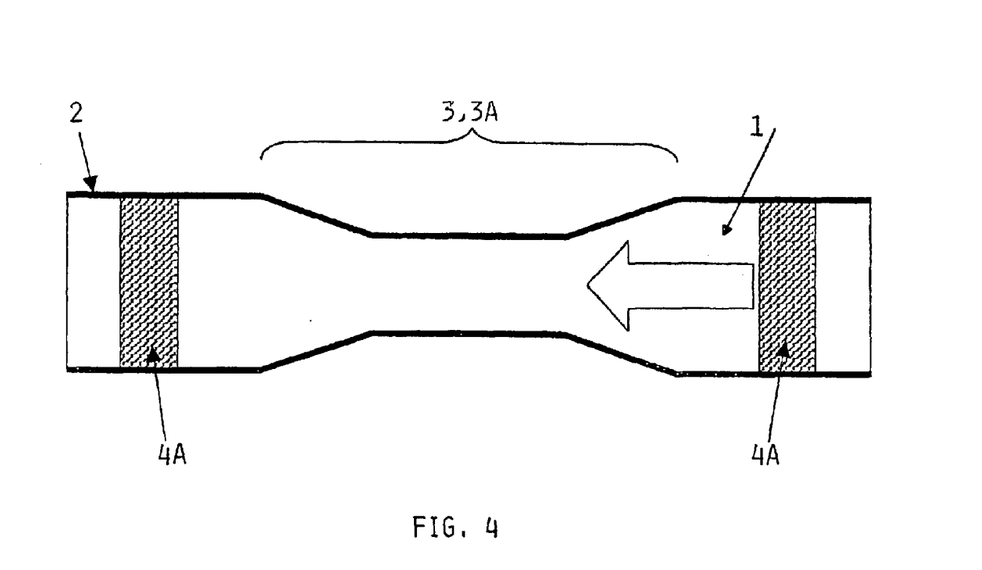
FIG. 4 A venturi tube with end grids in both ends in the pipe.

If the grids 4A are mounted in the pipe 2 on both sides of the throat, as shown in FIG. 4, there will appear resonance modes with most of the energy confined to the parts with the larger diameter on both sides between the grids and the throat. Depending on the relation between the resonant frequency, the cut-off frequency in the throat, and the length of the throat, the energies on both sides of the throat will be coupled to a larger or lesser degree. If they are strongly coupled, the energy will act like one single mode with two field maxima. In this case any inhomogeneity of the flow, for example liquid drops or gas bubbles, travelling through the resonator will cause two peaks in the time response. If the variations are large enough to give enough sensitivity, this phenomenon can be used for deriving the flow speed from the autocorrelation of the time response of the resonator. This redundancy in the speed measurement (autocorrelation in addition to DP measurement) can be used to increase the overall accuracy. If the coupling through the throat is very small, the cavities on both sides of the throat (bounded by the grids 4A and the throat) act like separate resonators. In this case it is most appropriate to use separate coupling probes for the two cavities. The speed can be derived from the cross-correlation of the time responses from the two resonators. Alternatively, if the extra speed measurement is not desired, it is sufficient to use only one grid on either side of the throat.

Figure 5:
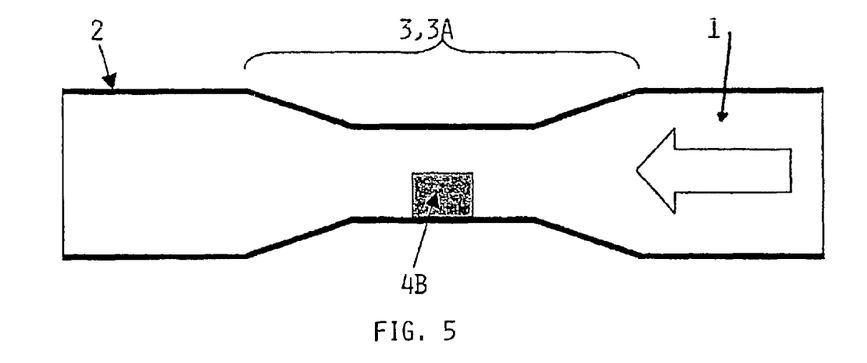
FIG. 5 A venturi tube with a fin resonator in the throat.

A microwave resonator can be implemented in a venturi tube using other structures than grids, as well. In one example an axial fin 4B is attached to the wall in a part of the throat, as shown in FIG. 5, the section with the fin 4B has a lower cut-off frequency than the rest of the throat, and will form a cylindrical fin resonator sensor [3], [6]. If the throat continues with unchanged diameter for a length equal to one inner diameter of the throat on both sides of the fin 4B (i.e. the total length of the narrow part of the throat is two diameters+the length of the fin 4B), the resonator will in practice be non-radiating and have a high quality factor [3]. For many practical purposes also a shorter narrow section will be good enough. For the length, height, and other design parameters of the fin 4B see [6].

Inverted Venturi

Figure 6:
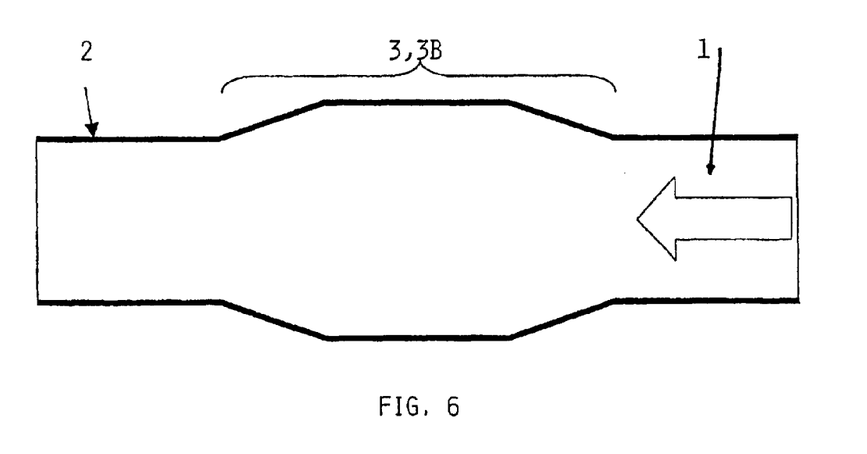
FIG. 6 An inverted venturi tube. The widened part of the pipe is also a microwave resonator.

If the meter is designed with an enlargement of the diameter of the pipe instead of a restriction, the structure will be an inverted venturi tube 3B, as illustrated in FIG. 6. The differential pressure generated by the flow in such a structure is also inverted compared to a venturi tube. The widened section 3B has a lower cut-off frequency for the microwaves than the main pipe 2. Because of the open ends it will support a TE mode with a resonant frequency $f_r = f_{cw}$, where $f_{cw}$ is the cut-off frequency of the widened section. Because $f_{cp} > f_{cw}$, where $f_{cp}$ is the cut-off frequency of the pipe, the energy can not escape. The widened section can therefore be used as both a microwave resonator sensor and an inverted venturi DP element.

Coaxial Structures

Figure 7:
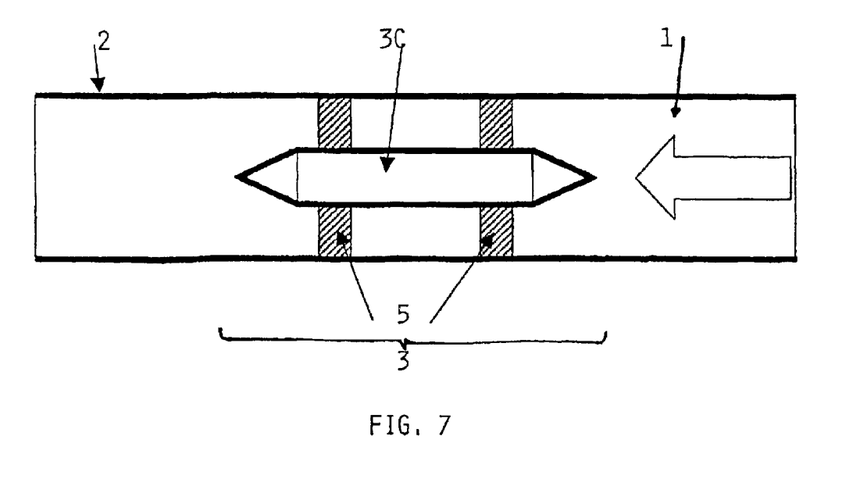
FIG. 7 A coaxial insert in the pipe. The structures holding the insert in place may be either dielectric, or made of a conducting material such that they form end grids for the resonator.

If a cylindrical metal body 3C is mounted in the center of the pipe 2 as shown in FIG. 7, the body 3C and the pipe 2 together form a coaxial structure, which supports a microwave TEM wave mode, which has no cut-off frequency, and the wavelength is the same as for a plane wave. The microwaves are reflected from the ends of the body thus creating a resonator. The body is held in place by support structures 5 in either both or one of the ends. The supports 5 may be either dielectric, or made of a conducting material such that they form end grids for the resonator. If a support 5 is made of metal (or some other electrically conducting material), the resonator is shorted in that end. If both ends are shorted by the supports, the first resonant frequency occurs, when the distance between the supports is $\lambda/2$, according to Eq. (7). The electric field maximum is midways between the supports. Also if the supports 5 are made of a non-conducting material, the resonance occurs at the frequency, where the body 3C is $\lambda/2$ long, according to Eq. (6). Now the electric field has mixima at the ends and a null midways between the end supports 5. The two separate maxima provide the possibility for also deriving the flow speed from the auto-correlation of a time series. If one support 5 is made of a conducting material and the other one of a non-conducting material (or is absent), the resonator will be $\lambda/4$ long, according to Eq. (8). The cylindrical body 3C reduces the cross sectional area and therefore creates a differential pressure related to the flow in the same way as a venturi tube. Of hydrodynamical reasons the ends of the body 3C should be tapered (e.g. conical) as shown in principle in FIG. 7.

Because the cylindrical body 3C creates both a microwave resonator and a DP element, the structure 3 can be used as a compact multiphase meter.

Orifice Plate

Figure 8:
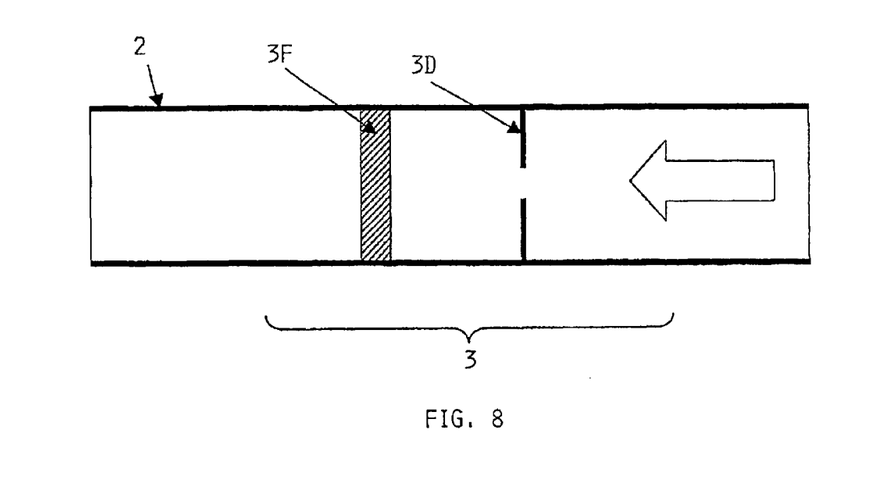
FIG. 8 An orifice plate with an end grid mounted downstream of the plate.

The orifice plate 3D is widely used as a DP element for measuring mainly gas flows, but can also be used for multiphase flows, at least for wet gas flows. If an end grid 3F is mounted on either side of the orifice plate, as shown in FIG. 8, the space between the orifice plate 3D and the end grid 3F is a microwave cavity. The structure 3 can therefore be used as a compact multiphase meter. For the design of the end grid 3F and the maximum size of the hole in the orifice plate 3D see [3].

Fin-V-cone

Figure 9:
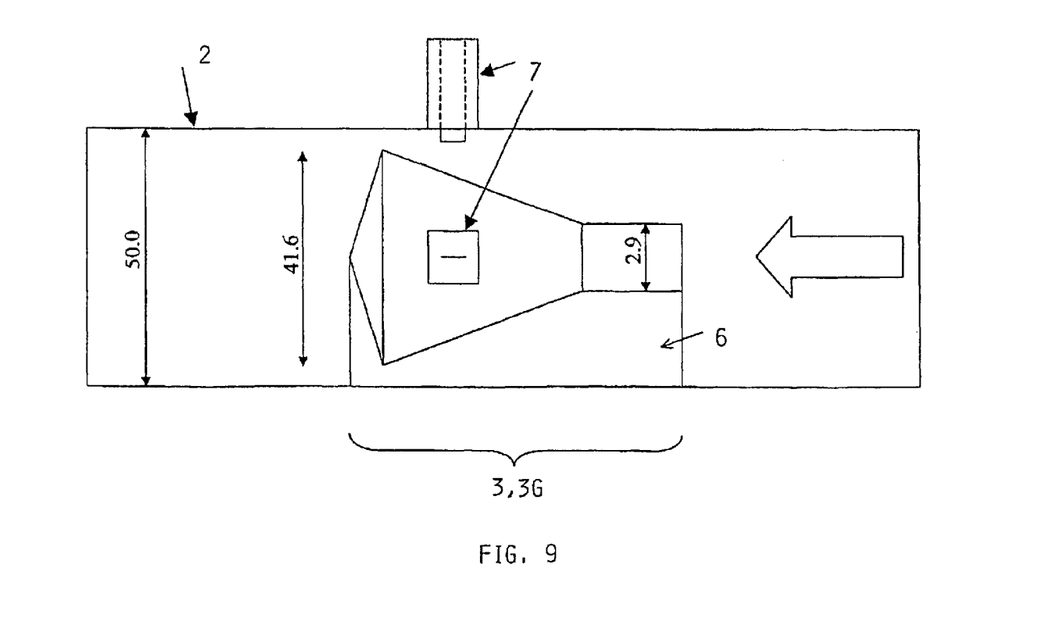
FIG. 9 V-cone with fin-like support along the whole length, here called Fin-V-cone. The given dimensions were used in the simulation described in the text.

In addition to the venturi tube and the orifice plate the V-cone 3G, as illustrated in FIG. 9, is a well-known DP element [10]. The V-cone also works well as a mixer of the fluid so that the measurements are virtually independent of the flow regime upstream of the meter. In one version of the invention the V-cone is attached to the pipe wall with a fin 6 extending over the whole length of the cone, as shown in FIG. 9. This version is a semisectorial structure [3] with a sector angle of 360° and a ratio of radii r=b/a (see FIG. 1) that varies along the structure. In this document this version is called a Fin-V-cone. The case with a uniform r was briefly described above. The Fin-V-cone is expected also to resonate at a frequency lower than the cut-off frequency of the pipe 2, but because of the nonuniform design (r varying along the resonator) it is difficult to theoretically predict the exact resonant frequency.

A sectorial or semisectorial resonator with open ends is expected to resonate at a frequency very close to the cut-off frequency [3]. One would intuitively expect the resonant frequency $f_r$ of the Fin-V-cone 3G to be primarily determined by the largest radius of the cone, which would give the lowest resonant frequency. If the 2" Fin-V-cone shown in FIG. 9 is used as an example, a=25 mm and b=20.8 mm. One then gets $$r = \frac{b}{a} = \frac{20.8}{25} = 0.832 \tag{10}$$

The cut-off frequency calculated using this value is a minimum limit for the predicted resonant frequency, because the cut-off frequency calculated for any other part of the V-cone gives a higher value. The so-called p-value for the lowest mode ($TE_{1/2,1}$) can be approximated by the polynomial (from Table 5.10a in [3]):

$$p'_{1/2,1} = 1.1657 - 1.7351r + 2.3644r^2 - 2.1955r^3 + 1.1584r^4 - 0.2579r^5 = 0.5490 \tag{11}$$

The minimum limit for the cut-off frequency can then be calculated from (Eq. (6.2) in [3]):

$$f_{c,1/2,1} = \frac{cp_{1/2,1}}{2\pi a} = 1.048 \text{ GHz} \tag{12}$$

Because this value is expected to be a coarse approximation, the structure was simulated using HFSS (High Frequency Structure Simulator—a software from Hewlett-Packard based on the finite element method). The simulation showed a frequency response with a resonance at 1.285 GHz, which is 22.6% higher than the estimated minimum limit. No other resonances were in the vicinity of this resonance, which makes it well suitable for measurement purposes. Based on the interpretation of the Fin-V-cone as a semisectorial structure the field can be expected to be concentrated to the narrow gap, where the diameter of the cone is largest, and to the side opposite to the fin. This was confirmed by the simulation. Because also the resonant frequency derived from the simulation was slightly higher than the minimum limit calculated from Eq. (12), as expected, the simulation confirmed that the Fin-V-cone works as a nonuniform semisectorial resonator.

Because the Fin-V-cone is known from previously to be a good DP element, and has now been shown also to be a good microwave resonator, the Fin-V-cone can be concluded to be a good example of the invention. Only one or two coupling probes need to be added to the Fin-V-cone to make it usable as a compact multiphase meter.

The fin 6 may be of varying thickness. It may have thicker portions comprising lead-ins for pressure tappings. If the pressure tappings are positioned in the wall of the pipe, the fin 6 may be thin all along its length.

Standard V-cone

Figure 10:
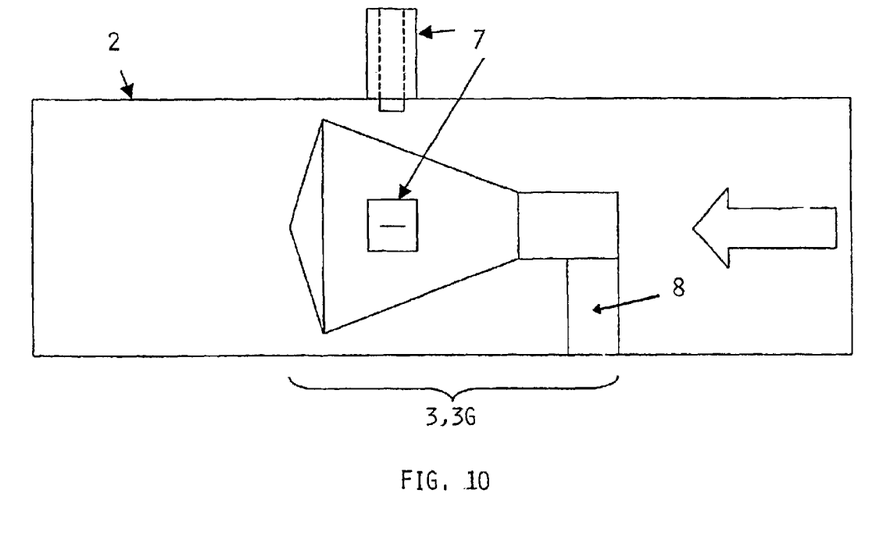
FIG. 10 Standard V-cone with one support. The given dimensions were used in the simulation described in the text, in addition to those given in FIG. 9.

A standard V-cone is attached to the pipe wall only in the thin end by a short support 8, as shown in FIG. 10. This structure can be expected to behave as a resonator, as well. The structure is not semisectorial, but resembles more the structure shown in FIG. 2. The current can be expected to be longitudinal (i.e. axial) in the cone and shorted to ground through the support. In the broad end of the cone the resonator is open-ended. According to Eq. (8) the first resonance should therefore be at the frequency where the structure is $\lambda/4$ long. However, because of the narrow gap between the cone and the pipe wall, the resonator is capacitively loaded in the open end. This will make the resonator look electrically longer leading to a lower resonant frequency than the one calculated from the physical length. The field in the narrow gap can be expected to be evenly distributed because of the coaxial geometry in that end. To verify this and to determine the resonant frequency of a standard V-cone more exactly, also the structure shown in FIG. 10 was simulated using HFSS. For the sake of simplicity the support was modelled as a short fin. The model was therefore identical to the one in FIG. 1, except for the length of the fin.

Interpreting the V-cone and the supporting fin as a $\lambda/4$ resonator, the length of the structure is 78 mm as measured along the centre line. If the capacitive loading is ignored, one gets a resonant frequency of 961 MHz. This is an upper limit because the capacitive loading from the cone to the pipe wall can be expected to reduce the frequency considerably. The simulation with HFSS confirmed the assumptions. Again a good resonance peak was displayed. The resonant frequency was 570 MHz. The simulation also showed the electric field to be uniformly distributed along the circumference, and axially to have a maximum concentrated to the narrow gap between the pipe wall and the widest part of the cone, as expected.

A physical model of a V-cone similar to the one in FIG. 10 has been built. The model was made of styrofoam and covered by aluminum foil. This was put inside a pipe with two coupling probes. The inner diameter of the sensor was 96 mm. The shape of the measured frequency response was very similar to the simulation result. The measured resonant frequency was 302 MHz, which reduced to correspond to a diameter of 50 mm, as simulated, gives 96/50*302=580 MHz. This is nearly identical to the simulation result, which gives confidence in the correctness of also the other simulation results.

Figure 12:
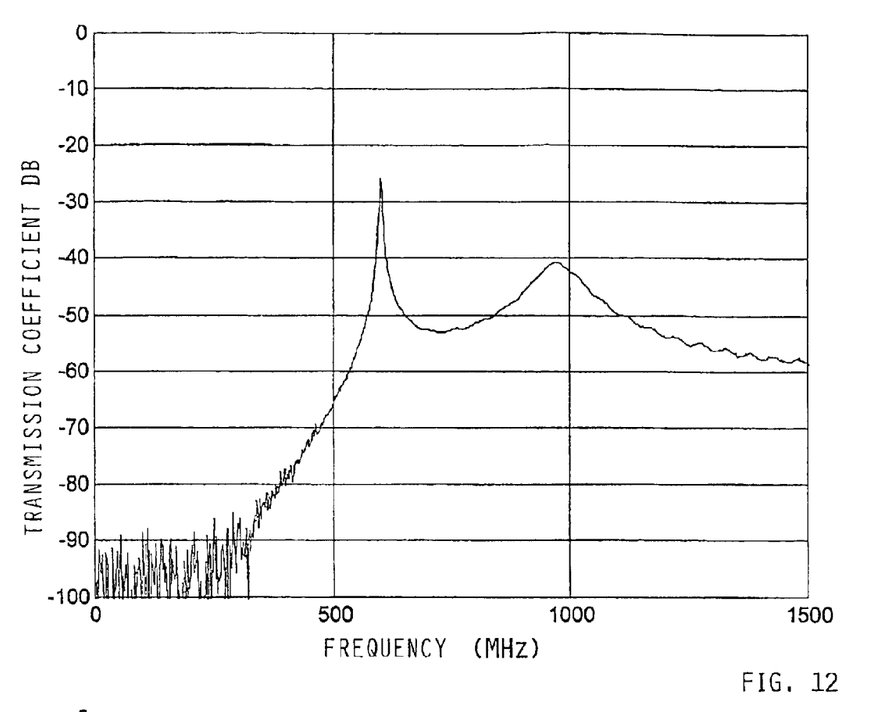
FIG. 12 The measured frequency response of the built 3" V-cone and microwave resonator sensor.

A real standard V-cone has also been built for a 3" pipe and with a cylindrical support, and with relative dimensions somewhat different from the model in FIG. 10. The measured resonant frequency of the air-filled sensor was 600 MHz. The measured corresponding frequency response is shown in FIG. 12. The wide hump to the right of the resonance peak is due to a resonance inside the probes, and can be eliminated by a small change in the design in future units. Even in the measured unit the hump does not interfere with the operation of the sensor due to the distance to the hump, the low and wide appearance of the hump, and the fact that the resonance peak only moves to the left, when a flow of fluid is measured.

Tests have been performed with the built standard V-cone unit in a test loop with dynamic flow. The results has shown show that the unit performs as expected both as a DP element and a microwave resonator.

Y-V-cone

The design of the standard V-cone, having only one support, intuitively seems sensitive to vibrations caused by turbulence. It would therefore seem preferable to have several, e.g. three supports (short fins or legs in an Y-formation with 120 degrees between the supports) instead of one to make the construction more robust. Increasing the number of supports will at the limit effectively turn the supports into a wall, where the V-cone is shorted. The structure will then be a coaxial resonator that is shorted in one end and open in the other. Compared to the standard V-cone shown in FIG. 10 the $\lambda/4$ resonator will therefore be foreshortened by one pipe radius and half of the width of the supports (25+9.7/2=29.8 mm), thus increasing the resonant frequency. If the effective length of the structure with one support is 131.6 mm ($\lambda/4$ at 570 MHz), the new effective length could be expected to be roughly 131.6−29.8=101.8 mm, giving a resonant frequency of 737 MHz.

The Y-V-cone (the structure with three supports) has been simulated with HFSS. The model of FIG. 10 was used and two more supports were added at angles of ±120° relative to the original support. The result showed that the resonant frequency has increased from 570 MHz to 774 MHz as a result of increasing the number of supports. Again the simple theoretical considerations produced qualitatively the right result, but failed to predict the resonant frequency accurately. The frequency response was good, showing no other resonances below 2.5 Ghz.

Bar-mounted V-cone

Figure 11:
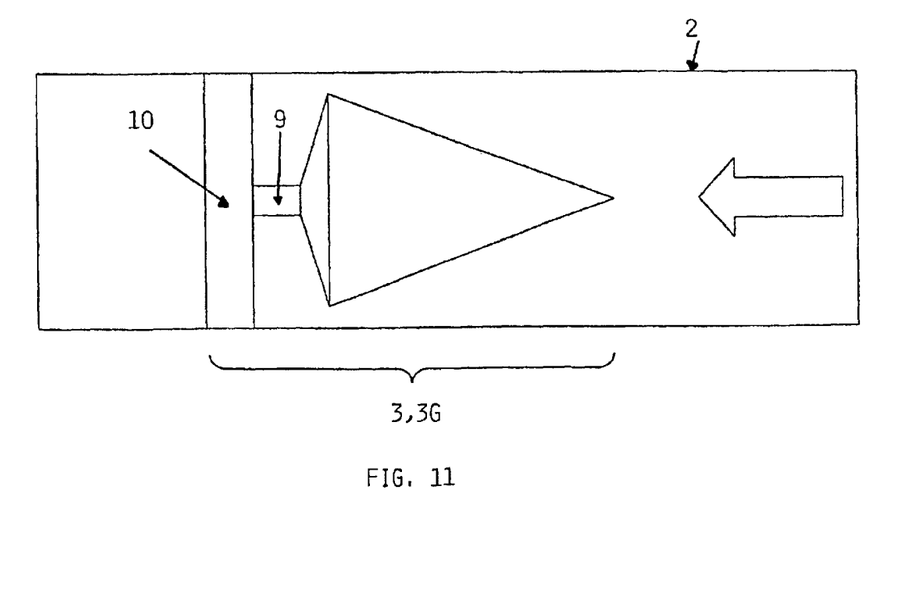
FIG. 11 Bar-mounted V-cone.

In another attachment scheme, the V-cone 3G may at the thick end be provided with one or more short taps 9. The taps are attached to one or more bars 10 attached to the inner wall of the pipe 2. In one example, as illustrated in FIG. 11 the tap(s) 9 may be a single short axial tap being attached to a single bar 10 positioned along a diameter of the cross-section of the pipe 2.

Coupling Probes

If coupling probes 7, as indicated in FIGS. 9 and 10, that couple to the electric field are used, they should preferably be located at the pipe wall close to the narrow gap between the cone and the wall, where the electric field strength is highest, and the best coupling therefore is achieved. Alternatively probes that couple to the magnetic field can be used, and should preferably be located close to the narrow end of the cone, where the magnetic field is strong. For more details on coupling probes see [2, Ch. 3].

V-cone Multiphase Meter

Above it was shown that a V-cone, with one support along the whole length of the cone or a part of it, or with several supports in the narrow end of the cone, can be used as a microwave resonator sensor. Because the V-cone also is a well-known DP element, only coupling probes have to be added to a V-cone to make it usable as a compact multiphase meter as described by the invention. In this basic configuration it is a water and hydrocarbon mass flow meter, which can be satisfactory for many applications, especially with wet gas flow. If combined with a PVT software package or a densitometer it becomes a full 3-phase multiphase meter.

Especially in wet gas flow the liquid tends to flow along the pipe wall in an annular flow regime. For many sensor designs the uneven distribution over the cross section may be a challenge or may cause the need for a separate mixer upstream of the sensor. A special advantage with the V-cone multiphase meter is that it also works as a mixer. The flow is accelerated in the narrow gap causing the liquid film to break up. In addition the electric field is evenly distributed in the whole gap making the sensor insensitive to how the fluid is distributed in the gap.

Although use of a PVT software package together with the V-cone unit is a preferable embodiment of the invention, it should be understood that the PVT software package could also be used in all types of apparatus according to the invention with the various types of implementations of the integrated mechanical structure as defined by the claims.

References

[1] Nyfors, E., A. Wee, "Measurement of mixtures of oil, water, and gas with microwave sensors. New developments and field experience of the MFI MultiPhase, and WaterCut Meters of Roxar", *Proc. Subsurface Sensing Technologies and Applications II, at SPIE's 45$^{th}$ Annual Meeting*, San Diego, July–August 2000, pp. 12–21, Invited.

[2] Nyfors, E., P. Vainikainen, *Industrial microwave sensors*, Artech House, Norwood, 1989, Chapter 1–3.

[3] Nyfors, E., *Cylindrical microwave resonator sensors for measuring materials under flow*, Thesis, Helsinki Univ. of Tech., Radio Lab. Report S243, May 2000, 181p.

[4] Collin, R. E., *Foundations for microwave engineering*, New York: McGraw-Hill, 1966, Chapter 7.

[5] Tiuri, M. E., E. G. Nyfors, P.-V. Vainikainen, S. H. Ståhl, Mittausmenetelmä ja -laite kiinteän, rakeisen aineen massavirtauksen ja kosteuden tai jonkin muun ominaisuuden määräämiseksi. (Method and device for measuring the material flow and the moisture, or some other property, of a solid, granular material; in Finnish), Suomi-Finland patent No. 69372, filed 30 Dec. 1983.

[6] Nyfors, E. G., Å. Bringsvor, Måler, særlig for kontinuerlig måling av blandingsforholdet mellom to fluider som strømmer i rør, f.eks. vanninnhold i olje; samt fremgangsmåte for gjennomføring av slik måling. (Meter, especially for the continuous measurement of the mixing ratio of two fluids flowing in a pipe; and method for performing such measurements; in Norwegian), Norwegian patent No. 308.922, Filed Jun. 3, 1998.

[7] Nyfors, E., A method for measuring properties of flowing fluids, and a metering device and a sensor used for performing this method, Norwegian patent application No. 2000.2511, filed May 15, 2000.

[8] Gaisford, S. G., J. P. Watjen, B. G. Bjørnsen, Composition monitor and monitoring process using impedance measurements, U.S. Pat. No. 5,103,181. Filed Oct. 5, 1988.

[9] International standard ISO 5167-1: Measurement of fluid flow by means of pressure differential devices.

[10] McCall, F., Fluid flowmeter, U.S. Pat. No. 4,638,672, filed Sep. 11, 1984.

[11] Chisholm, D., *Two-Phase flow in pipelines and heat exchangers*, Longman Inc. New York, 1983, Chapter 11.

What is claimed is:

1. Apparatus for measuring composition and flow rate properties of a fluid (1) comprising a mixture of e.g. oil and water in a pipe (2), wherein an integrated mechanical structure (3) serves as a microwave resonator sensor and as a differential pressure element for providing permittivity and flow rate measurements, respectively, wherein an external excitation circuit is provided for generating a microwave field in the microwave resonator sensor, and wherein there are provided microwave probes and a differential pressure measuring element having outputs connected to inputs of a microprocessor or calculating means for determining a property of the flow, and comprising means for determining a resonance frequency of the microwave resonator sensor and the dielectric permittivity of the fluid.

2. Apparatus according to claim 1 for measurement of a fluid (1) comprising also a gas, wherein the apparatus further comprises a densitometer for providing density measurements in the fluid.

3. Apparatus according to claim 1 for measurement of a fluid (1) comprising also a hydrocarbon gas being in thermodynamic equilibrium with the oil, wherein the apparatus further comprises a PVT-software program running on a computer or microprocessor unit for providing a calculation of how the hydrocarbon content is divided between a liquid(oil) phase and a gas phase.

4. Apparatus according to claim 1, wherein the microwave resonator is a cavity resonator.

5. Apparatus according to claim 1, wherein the integrated mechanical structure (3) comprises a portion of the pipe being formed as a Venturi tube (3A), the structure (3) further comprising additional mechanical element(s) (4) enabling the Venturi tube (3A) to operate as a microwave cavity resonator.

6. Apparatus according to claim 5, wherein the additional mechanical element(s) (4) comprise(s) grid(s) (4A) mounted at one or both ends of the Venturi tube.

7. Apparatus according to claim 6, wherein the grids (4A) are mounted in a throat (narrow part) of the Venturi tube (3A).

8. Apparatus according to claim 6, wherein the grids (4A) are mounted in the pipe on both sides of a throat (narrow part) of the Venturi tube (3A).

9. Apparatus according to claim 5, wherein the additional mechanical element(s) (4) comprise(s) an axial fin (4B) attached to an inside wall of the throat (narrow part) of the Venturi tube (3A).

10. Apparatus according to claim 1, wherein the integrated mechanical structure (3) comprises a widened section of the pipe forming an inverted Venturi tube (3B) thus providing a microwave cavity resonating at a frequency below the cutoff frequency of the unwidened pipe.

11. Apparatus according to claim 1, wherein the integrated mechanical structure (3) comprises a coaxial structural element (3C) mounted in the center of the pipe.

12. Apparatus according to claim 11, wherein the coaxial structural element (3C) is mounted with end supports (5) at least one of which are made of a dielectric material.

13. Apparatus according to claim 11, wherein the coaxial structural element (3C) is mounted with end supports (5) at least one of which are made of a conducting material.

14. Apparatus according to claim 12, wherein the end supports (5) are in the form of grids.

15. Apparatus according to claim 1, wherein the integrated mechanical structure (3) comprises an orifice plate (3D) and an end grid (3F).

16. Apparatus according to claim 1, wherein the integrated mechanical structure (3) comprises a V-cone (3G) being attached to the wall of the pipe (2) using attachment means (6).

17. Apparatus according to claim 16, wherein the attachment means (6) comprises one or more fins (6) attached to part(s) of or the whole of the length of the cone.

18. Apparatus according to claim 16, wherein the attachment means (6) comprises one or more radially equidistantly spaced parts, for example fins.

19. Apparatus according to claim 16, wherein the attachment means (6) comprises one or more taps (9) mounted at the thick end of the cone, the taps being attached to one or more bars (10), the bars being attached to the inside wall of the pipe (2).

20. Apparatus according to claim 1, wherein the apparatus comprises means for determining a resonance frequency of the microwave cavity and hence a real part of the dielectric permittivity of the fluid in the cavity, means for determining a quality factor of the resonance of the microwave cavity, and means for using the resonance frequency and the quality factor to obtain an estimate of the salinity of the possible water in the fluid.

21. Apparatus according to claim 20, wherein the estimate of salinity of the possible water or possible changes thereof is used as an indicator of when the well starts to produce formation water.

22. Apparatus according to claim 1, wherein the integrated mechanical structure (3) forms a combined single structure.

* * * * *